(12) United States Patent
Lee et al.

(10) Patent No.: US 9,156,754 B2
(45) Date of Patent: *Oct. 13, 2015

(54) PROCESS TO RECOVER ALCOHOL WITH REDUCED WATER FROM OVERHEAD OF ACID COLUMN

(71) Applicant: Celanese International Corporation, Irving, TX (US)

(72) Inventors: David Lee, Seabrook, TX (US); Adam Orosco, Houston, TX (US); Claudio Ribeiro, Houston, TX (US); R. Jay Warner, Houston, TX (US); Robert Alan Deck, Richmond, TX (US); Emily Duff, League City, TX (US); Victor J. Johnston, Houston, TX (US)

(73) Assignee: Celanese International Corporation, Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/571,423

(22) Filed: Dec. 16, 2014

(65) Prior Publication Data

US 2015/0099905 A1    Apr. 9, 2015

Related U.S. Application Data

(63) Continuation of application No. 13/457,280, filed on Apr. 26, 2012, now Pat. No. 8,927,788, and a continuation-in-part of application No. 13/094,588, filed on Apr. 26, 2011, now Pat. No. 8,686,200, and a continuation-in-part of application No. 13/292,914, filed on Nov. 9, 2011, now Pat. No. 8,927,784.

(51) Int. Cl.
| | | |
|---|---|---|
| *C07C 29/149* | (2006.01) | |
| *C07C 29/80* | (2006.01) | |
| *C07C 67/08* | (2006.01) | |
| *C07C 67/54* | (2006.01) | |
| *C07C 51/12* | (2006.01) | |
| *C07C 29/76* | (2006.01) | |
| *C07C 29/84* | (2006.01) | |
| *C10L 1/02* | (2006.01) | |

(52) U.S. Cl.
CPC ............ *C07C 29/149* (2013.01); *C07C 29/76* (2013.01); *C07C 29/80* (2013.01); *C07C 29/84* (2013.01); *C07C 51/12* (2013.01); *C07C 67/08* (2013.01); *C07C 67/54* (2013.01); *C10L 1/02* (2013.01); *C10L 2200/04* (2013.01); *C10L 2290/543* (2013.01); *C10L 2290/548* (2013.01)

(58) Field of Classification Search
CPC ........ C07C 29/149; C07C 29/80; C07C 27/04
USPC .................................. 568/885, 913, 918
See application file for complete search history.

(56) References Cited

U.S. PATENT DOCUMENTS

| | | |
|---|---|---|
| 2,607,807 A | 8/1952 | Ford |
| 2,649,407 A | 8/1953 | Harrison et al. |
| 2,702,783 A | 2/1955 | Harrison et al. |
| 2,801,209 A | 7/1957 | Muller et al. |
| 2,882,244 A | 4/1959 | Milton |
| 3,102,150 A | 8/1963 | Hunter et al. |
| 3,130,007 A | 4/1964 | Breck |
| 3,408,267 A | 10/1968 | Miller et al. |
| 3,445,345 A | 5/1969 | Katzen et al. |
| 3,478,112 A | 11/1969 | Karl et al. |
| 3,769,329 A | 10/1973 | Knox et al. |
| 3,990,952 A | 11/1976 | Katzen et al. |
| 4,126,539 A | 11/1978 | Derr, Jr. et al. |
| 4,149,940 A | 4/1979 | Pinto |
| 4,275,228 A | 6/1981 | Gruffaz et al. |
| 4,306,942 A | 12/1981 | Brush et al. |
| 4,317,918 A | 3/1982 | Takano et al. |
| 4,319,058 A | 3/1982 | Kulpranthipanja et al. |
| 4,352,940 A | 10/1982 | Adelman et al. |
| 4,379,028 A | 4/1983 | Berg et al. |
| 4,395,576 A | 7/1983 | Kwantes et al. |
| 4,398,039 A | 8/1983 | Pesa et al. |
| 4,421,939 A | 12/1983 | Kiff et al. |
| 4,422,903 A | 12/1983 | Messick et al. |
| 4,443,639 A | 4/1984 | Pesa et al. |
| 4,454,358 A | 6/1984 | Kummer et al. |
| 4,465,854 A | 8/1984 | Pond et al. |
| 4,471,136 A | 9/1984 | Larkins et al. |

(Continued)

FOREIGN PATENT DOCUMENTS

| | | |
|---|---|---|
| CN | 101519349 | 9/2009 |
| CN | 201768393 | 3/2011 |

(Continued)

OTHER PUBLICATIONS

Alcala, et al., (2005). Experimental and DFT studies of the conversion of ethanol and acetic acid on PtSn-based catalysts, Journal of Physical Chemistry, 109(6), 2074-2085.

Amit M. Goda et al., DFT modeling of selective reduction of acetic acid to acetaldehyde on Pt-based bimetallic catalysts, 20th NAM, Houston, TX, Jun. 17-22, 2007 available online at <http://www.nacatsoc.org/20nam/abstracts/O-S9-18.pdf>.

Anonymous: "Studies in Extractive and Azeotropic Distillation Series; Study No. 4—Separation of Alcohols from the Acetate/Alcohol/Water Ternary by Extractive Distillation" May 9, 2008, pp. 1-9.

Benson, Tracy J., et al., "Cellulose Based Adsorbent Materials for the Dehydration of Ethanol Using Thermal Swing Adsorption", Adsorption, Kluwer Academic Publishers, vol. 11, No. 1, Jul. 1, 2005, pp. 697-701.

(Continued)

*Primary Examiner* — Elvis O Price

(74) *Attorney, Agent, or Firm* — Kilpatrick Townsend & Stockton LLP

(57) ABSTRACT

A process for recovering ethanol obtained from the hydrogenation of acetic acid. The crude ethanol product is separated in a column to produce a distillate stream comprising acetaldehyde and ethyl acetate and a residue stream comprising ethanol, acetic acid, ethyl acetate and water. The ethanol product is recovered from the residue stream.

20 Claims, 5 Drawing Sheets

(56) References Cited

U.S. PATENT DOCUMENTS

| | | |
|---|---|---|
| 4,480,115 A | 10/1984 | McGinnis |
| 4,492,808 A | 1/1985 | Hagen et al. |
| 4,497,967 A | 2/1985 | Wan |
| 4,517,391 A | 5/1985 | Schuster et al. |
| 4,520,213 A | 5/1985 | Victor |
| 4,541,897 A | 9/1985 | Sommer et al. |
| 4,559,109 A | 12/1985 | Lee et al. |
| 4,569,726 A | 2/1986 | Berg et al. |
| 4,626,321 A | 12/1986 | Grethlein et al. |
| 4,654,123 A | 3/1987 | Berg et al. |
| 4,678,543 A | 7/1987 | Houben et al. |
| 4,692,218 A | 9/1987 | Houben et al. |
| 4,777,303 A | 10/1988 | Kitson et al. |
| 4,804,791 A | 2/1989 | Kitson et al. |
| 4,826,795 A | 5/1989 | Kitson et al. |
| 4,842,693 A | 6/1989 | Wheldon |
| 4,880,937 A | 11/1989 | Matsushita et al. |
| 4,886,905 A | 12/1989 | Larkins et al. |
| 4,908,477 A | 3/1990 | Hartmann et al. |
| 4,961,826 A | 10/1990 | Grethlein et al. |
| 4,978,778 A | 12/1990 | Isshiki et al. |
| 4,985,572 A | 1/1991 | Kitson et al. |
| 4,990,655 A | 2/1991 | Kitson et al. |
| 4,994,608 A | 2/1991 | Torrence et al. |
| 5,001,259 A | 3/1991 | Smith et al. |
| 5,026,908 A | 6/1991 | Smith et al. |
| 5,035,776 A | 7/1991 | Knapp |
| 5,061,671 A | 10/1991 | Kitson et al. |
| 5,070,016 A | 12/1991 | Hallberg et al. |
| 5,124,004 A | 6/1992 | Grethlein et al. |
| 5,144,068 A | 9/1992 | Smith et al. |
| 5,149,680 A | 9/1992 | Kitson et al. |
| 5,185,481 A | 2/1993 | Muto et al. |
| 5,198,592 A | 3/1993 | Van Beijnum et al. |
| 5,215,902 A | 6/1993 | Tedder |
| 5,227,141 A | 7/1993 | Kim et al. |
| 5,233,099 A | 8/1993 | Tabata et al. |
| 5,237,108 A | 8/1993 | Marraccini et al. |
| 5,250,271 A | 10/1993 | Horizoe et al. |
| 5,348,625 A | 9/1994 | Berg |
| 5,414,161 A | 5/1995 | Uhm et al. |
| 5,415,741 A | 5/1995 | Berg |
| 5,426,246 A | 6/1995 | Nagahara et al. |
| 5,437,770 A | 8/1995 | Berg |
| 5,445,716 A | 8/1995 | Berg |
| 5,449,440 A | 9/1995 | Rescalli et al. |
| 5,502,248 A | 3/1996 | Funk et al. |
| RE35,377 E | 11/1996 | Steinberg et al. |
| 5,599,976 A | 2/1997 | Scates et al. |
| 5,762,765 A | 6/1998 | Berg |
| 5,770,770 A | 6/1998 | Kim et al. |
| 5,800,681 A | 9/1998 | Berg |
| 5,821,111 A | 10/1998 | Grady et al. |
| 5,861,530 A | 1/1999 | Atkins et al. |
| 5,973,193 A | 10/1999 | Crane et al. |
| 5,993,610 A | 11/1999 | Berg |
| 6,040,474 A | 3/2000 | Jobson et al. |
| 6,093,845 A | 7/2000 | Van Acker et al. |
| 6,121,498 A | 9/2000 | Tustin et al. |
| 6,143,930 A | 11/2000 | Singh et al. |
| 6,232,352 B1 | 5/2001 | Vidalin et al. |
| 6,294,703 B1 | 9/2001 | Hara et al. |
| 6,326,515 B1 | 12/2001 | Clode et al. |
| 6,375,807 B1 | 4/2002 | Nieuwoudt et al. |
| 6,444,842 B1 | 9/2002 | Gerberich et al. |
| 6,458,996 B1 | 10/2002 | Muskett |
| 6,462,231 B1 | 10/2002 | Yanagawa et al. |
| 6,472,555 B2 | 10/2002 | Choudary et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,627,770 B1 | 9/2003 | Cheung et al. |
| 6,632,330 B1 | 10/2003 | Colley et al. |
| 6,657,078 B2 | 12/2003 | Scates et al. |
| 6,673,978 B2 | 1/2004 | Coute et al. |
| 6,685,754 B2 | 2/2004 | Kindig et al. |
| 6,693,213 B1 | 2/2004 | Kolena et al. |
| 6,696,596 B1 | 2/2004 | Herzog et al. |
| 6,723,886 B2 | 4/2004 | Allison et al. |
| 6,755,975 B2 | 6/2004 | Vane et al. |
| 6,765,110 B2 | 7/2004 | Warner et al. |
| 6,768,021 B2 | 7/2004 | Horan et al. |
| 6,809,217 B1 | 10/2004 | Colley et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,074,603 B2 | 7/2006 | Verser et al. |
| 7,084,312 B1 | 8/2006 | Huber et al. |
| 7,115,772 B2 | 10/2006 | Picard et al. |
| 7,208,624 B2 | 4/2007 | Scates et al. |
| 7,223,886 B2 | 5/2007 | Scates et al. |
| 7,226,886 B2 | 6/2007 | Jayaratne et al. |
| 7,297,236 B1 | 11/2007 | Vander Griend et al. |
| 7,351,559 B2 | 4/2008 | Verser et al. |
| 7,399,892 B2 | 7/2008 | Rix et al. |
| 7,507,562 B2 | 3/2009 | Verser et al. |
| 7,553,397 B1 | 6/2009 | Colley et al. |
| 7,572,353 B1 | 8/2009 | Vander Griend |
| 7,601,865 B2 | 10/2009 | Verser et al. |
| 7,608,744 B1 | 10/2009 | Johnston et al. |
| 7,682,812 B2 | 3/2010 | Verser et al. |
| 7,700,814 B2 | 4/2010 | Garton et al. |
| 7,732,173 B2 | 6/2010 | Mairal et al. |
| 7,744,727 B2 | 6/2010 | Blum et al. |
| 7,834,223 B2 | 11/2010 | Atkins |
| 7,842,844 B2 | 11/2010 | Atkins |
| 7,863,489 B2 | 1/2011 | Johnston et al. |
| 7,884,253 B2 | 2/2011 | Stites et al. |
| 7,888,082 B2 | 2/2011 | Verser et al. |
| 7,906,680 B2 | 3/2011 | Scates et al. |
| 7,947,746 B2 | 5/2011 | Daniel et al. |
| 8,071,821 B2 | 12/2011 | Johnston et al. |
| 8,378,153 B2 | 2/2013 | Daniel et al. |
| 8,394,985 B2 | 3/2013 | Johnston et al. |
| 8,425,733 B2 | 4/2013 | Halvorsen et al. |
| 8,502,001 B2 | 8/2013 | Daniel et al. |
| 8,524,954 B2 | 9/2013 | Ditzel et al. |
| 8,604,255 B2 | 12/2013 | Sarager et al. |
| 8,669,400 B2 | 3/2014 | Johnston et al. |
| 8,829,250 B2 | 9/2014 | Sarager et al. |
| 8,846,988 B2 | 9/2014 | Jevtic et al. |
| 8,884,080 B2 | 11/2014 | Lee et al. |
| 8,907,140 B2 | 12/2014 | Daniel et al. |
| 2003/0013908 A1 | 1/2003 | Horan et al. |
| 2003/0077771 A1 | 4/2003 | Verser et al. |
| 2005/0197506 A1 | 9/2005 | Scates et al. |
| 2006/0019360 A1 | 1/2006 | Verser et al. |
| 2006/0106246 A1 | 5/2006 | Warner et al. |
| 2006/0127999 A1 | 6/2006 | Verser et al. |
| 2007/0031954 A1 | 2/2007 | Mairal et al. |
| 2007/0106246 A1 | 5/2007 | Modesitt |
| 2007/0238605 A1 | 10/2007 | Strehlau et al. |
| 2007/0270511 A1 | 11/2007 | Melnichuk et al. |
| 2008/0135396 A1 | 6/2008 | Blum |
| 2008/0193989 A1 | 8/2008 | Verser et al. |
| 2008/0207953 A1 | 8/2008 | Houssin et al. |
| 2008/0210540 A1 | 9/2008 | Dieterle et al. |
| 2009/0005588 A1 | 1/2009 | Hassan et al. |
| 2009/0014313 A1 | 1/2009 | Lee et al. |
| 2009/0023192 A1 | 1/2009 | Verser et al. |
| 2009/0069609 A1 | 3/2009 | Kharas et al. |
| 2009/0081749 A1 | 3/2009 | Verser et al. |
| 2009/0166172 A1 | 7/2009 | Casey et al. |
| 2009/0221725 A1 | 9/2009 | Chorney et al. |
| 2009/0270651 A1 | 10/2009 | Zinobile et al. |
| 2009/0274480 A1 | 11/2009 | Zona |
| 2009/0281354 A1 | 11/2009 | Mariansky et al. |
| 2009/0299092 A1 | 12/2009 | Beavis et al. |
| 2009/0318573 A1 | 12/2009 | Stites et al. |
| 2009/0326080 A1 | 12/2009 | Chornet et al. |
| 2010/0016454 A1 | 1/2010 | Gracey et al. |
| 2010/0029980 A1 | 2/2010 | Johnston et al. |
| 2010/0029995 A1 | 2/2010 | Johnston et al. |
| 2010/0030001 A1 | 2/2010 | Chen et al. |

(56) References Cited

U.S. PATENT DOCUMENTS

| | | |
|---|---|---|
| 2010/0030002 A1 | 2/2010 | Johnston et al. |
| 2010/0121114 A1 | 5/2010 | Johnston et al. |
| 2010/0137630 A1 | 6/2010 | Garton et al. |
| 2010/0197485 A1 | 8/2010 | Johnston et al. |
| 2010/0197959 A1 | 8/2010 | Johnston et al. |
| 2010/0197985 A1 | 8/2010 | Johnston et al. |
| 2010/0204512 A1 | 8/2010 | Kimmich et al. |
| 2011/0004033 A1 | 1/2011 | Johnston et al. |
| 2011/0046421 A1 | 2/2011 | Daniel et al. |
| 2011/0082322 A1 | 4/2011 | Jevtic et al. |
| 2011/0098501 A1 | 4/2011 | Johnston et al. |
| 2011/0185628 A1 | 8/2011 | Johnston et al. |
| 2011/0190547 A1 | 8/2011 | Jevtic et al. |
| 2011/0190548 A1 | 8/2011 | Jevtic et al. |
| 2011/0275861 A1 | 11/2011 | Johnston et al. |
| 2011/0275862 A1 | 11/2011 | Johnston et al. |
| 2011/0275864 A1 | 11/2011 | Warner et al. |
| 2012/0010437 A1 | 1/2012 | Jevtic |
| 2012/0010438 A1 | 1/2012 | Lee et al. |
| 2012/0010439 A1 | 1/2012 | Jevtic |
| 2012/0010440 A1 | 1/2012 | Sarager |
| 2012/0010445 A1 | 1/2012 | Johnston et al. |
| 2012/0010446 A1 | 1/2012 | Warner et al. |
| 2012/0273338 A1 | 11/2012 | Lee et al. |
| 2012/0277481 A1 | 11/2012 | Warner |
| 2012/0277497 A1 | 11/2012 | Lee et al. |
| 2012/0323049 A1 | 12/2012 | Lee |
| 2012/0323050 A1 | 12/2012 | Lee |
| 2013/0217925 A1 | 8/2013 | Chornet et al. |
| 2014/0039225 A1 | 2/2014 | Daniel et al. |
| 2014/0094629 A1 | 4/2014 | Sarager et al. |

FOREIGN PATENT DOCUMENTS

| | | |
|---|---|---|
| CN | 102228831 | 11/2011 |
| CN | 102229520 | 11/2011 |
| EP | 0056488 A2 | 7/1982 |
| EP | 0104197 | 4/1984 |
| EP | 0137749 | 4/1985 |
| EP | 0167300 | 1/1986 |
| EP | 0175558 | 3/1986 |
| EP | 0192587 | 8/1986 |
| EP | 0400904 | 5/1990 |
| EP | 0372847 | 6/1990 |
| EP | 0198682 B1 | 3/1991 |
| EP | 0285420 B1 | 5/1991 |
| EP | 0456647 | 11/1991 |
| EP | 0285786 B1 | 5/1993 |
| EP | 0990638 A1 | 4/2000 |
| EP | 2060553 | 5/2009 |
| EP | 2060555 A1 | 5/2009 |
| EP | 2072487 | 6/2009 |
| EP | 2072488 | 6/2009 |
| EP | 2072489 A1 | 6/2009 |
| EP | 2072492 | 6/2009 |
| EP | 2186787 A1 | 5/2010 |
| JP | 4-193304 | 7/1992 |
| JP | 6-116182 | 4/1994 |
| JP | 2001-046874 | 2/2001 |
| WO | WO 83/03409 | 10/1983 |
| WO | 02/092541 A1 | 11/2002 |
| WO | 2005/102513 A1 | 11/2005 |
| WO | 2007/003897 A1 | 1/2007 |
| WO | WO 2008/135192 | 11/2008 |
| WO | WO 2009/009320 | 1/2009 |
| WO | WO 2009/009322 | 1/2009 |
| WO | WO 2009/009323 | 1/2009 |
| WO | 2009/048335 A1 | 4/2009 |
| WO | 2009/063174 A1 | 5/2009 |
| WO | 2009/063176 A1 | 5/2009 |
| WO | 2009/105960 A1 | 9/2009 |
| WO | 2010/014151 A2 | 2/2010 |
| WO | 2010/055285 A1 | 5/2010 |
| WO | WO 2011/053365 | 5/2011 |
| WO | 2011/097227 A2 | 8/2011 |
| WO | WO 2011/097193 | 8/2011 |
| WO | WO 2011/097219 | 8/2011 |
| WO | WO 2011/097220 | 8/2011 |
| WO | 2011/140485 A1 | 11/2011 |
| WO | 2012/006219 A2 | 1/2012 |
| WO | 2012/006228 A1 | 1/2012 |
| WO | 2012/006499 A2 | 1/2012 |

OTHER PUBLICATIONS

Calvar, et al., "Esterification of acetic acid and ethanol: Reaction kinetics and operation in a packed bed reactive distillation column", Chem Engineering and Processing, vol. 46, No. 12, Oct. 9, 2007, pp. 1317-1323.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

H. Constantin et al., "Influence of C-Sources on the Denitrification Rate of a High-Nitrate Concentrated Industrial Wastewater", Wat. Res. vol. 31, No. 3, 1997, pp. 583-589.

Hilmen, Separation of Azeotropic Mixtures: Tools for Analysis and Studies on Batch Distillation Operation (Nov. 2000) p. 17-20.

Huang, et al., "Low-Energy Distillation-Membrane separation process", Industrial & Engineering Chemistry Research, Am. Chem. Soc., vol. 49, No. 8, Jan. 1, 2010, pp. 3760-3768.

J. Jones, et al., Platinum Metals Review, vol. 44, No. 3, pp. 94-104 (Jul. 2000).

Jakobsson, et al., "Modelling of a side reactor configuration combining reaction and distillation", Chemical Engineering Science, vol. 57, No. 9, May 1, 2002, pp. 1521-1524.

Kita H., et al., "Synthesis of a Zeolite NAA Membrane for Pervaporation of Water/Organic Liquid Mixtures", Journal of Materials Science Letters, vol. 14, Jan. 1, 1995, pp. 206-208.

Marian Simo, et al., "Adsorption/Desorption of Water and Ethanol on 3A Zeolite in Neo-Adiabatic Fixed Bed", Industrial and Engineering Chemistry Research, vol. 48, No. 20, Sep. 25, 2009, pp. 9247-9260.

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Rachmady, Acetic Acid Reduction by H2 on Bimetallic Pt-Fe Catalysts, Journal of Catalysis 209, 87-98 (Apr. 1, 2002), Elsevier Science (USA).

Santori et al.(2000). Hydrogenation of carbonylic compounds on Pt/SiO2 catalysts modified with SnBu4, Studies in Surface Science and Catalysis, 130, 2063-2068.

Spivey et al., "Heterogeneous catalytic synthesis of ethanol from biomass-dervied syngas," Chemical Society Review, 2007, vol. 36, pp. 1514-1528.

Subramani et al., "A Review of Recent Literature to Search for an Efficient Catalytic Process for the Conversion of Syngas to Ethanol," Energy & Fuels, 2008, vol. 22, pp. 814-839.

V. Ragaini et al., "Increasing the value of dilute acetic acid streams through esterification Part 1. Experimental analysis of the reaction zone", Applied Catalysis B: Environmental, vol. 64, 2006, pp. 66 -71.

Waterland, et al., "Safety and Performance Assessment of Ethanol/Diesel Blends (e-blend)", NREL/SR-540-34817, at p. 1-1, Sep. 2003.

Xu, et al., "Kinetics of acetic acid esterification over ion exchange catalysts", Canadian Journal of Chemical Engineering, vol. 74, Aug. 1, 1996, pp. 493-500.

Y. Zhu, et al., "Techno-economic Analysis for the Thermochemical Conversion of Lignocellulosic Biomass to Ethanol via Acetic Acid Synthesis", Apr. 1, 2009, pp. 1-71.

ZeaChem, Inc., Technology Overview, Lakewood, Colorado www.zeachem.com, 2008.

Zheng, et al., (2007). Preparation and catalytic properties of a bimetallic Sn-Pt complex in the supercages of NaY zeolite by use of surface organometallic chemistry, Applied Organometallic Chemistry, 21(10), 836-840.

International Search Report and Written Opinion for PCT/US2012/035273 mailed Jul. 30, 2012.

Office Action for Chinese Appl. No. 201280003023.7 dated Dec. 12, 2014.

(56) References Cited

OTHER PUBLICATIONS

International Search Report and Written Opinion for PCT/US2011/023276 mailed Sep. 2, 2011.
International Search Report and Written Opinion for PCT/US2011/060014 mailed Jun. 29, 2012.
International Search Report and Written Opinion for PCT/US2012/035196 mailed Aug. 6, 2012.
International Search Report and Written Opinion for PCT/US2011/060019 mailed Apr. 19, 2012.
International Search Report and Written Opinion for PCT/US2011/059889 mailed Jul. 6, 2012.
International Search Report and Written Opinion for PCT/US2012/035203 mailed Jul. 11, 2012.
International Search Report and Written Opinion for PCT/US2012/035189 mailed Jul. 30, 2012.
International Search Report and Written Opinion for PCT/US2012/035220 mailed Aug. 2, 2012.
International Search Report and Written Opinion for PCT/US2012/035208 mailed Nov. 9, 2012.
International Search Report and Written Opinion for PCT/US2012/035271 mailed Nov. 12, 2012.
International Search Report and Written Opinion for PCT/US2012/035194 mailed Nov. 15, 2012.
International Search Report and Written Opinion for PCT/US2012/035175 mailed Nov. 15, 2012.
International Search Report and Written Opinion for PCT/US2012/035198 mailed Oct. 30, 2012.
Office Action for corresponding Chinese Appl. No. 201280003023.7 dated May 12, 2014.

PROCESS TO RECOVER ALCOHOL WITH REDUCED WATER FROM OVERHEAD OF ACID COLUMN

CROSS REFERENCE TO RELATED APPLICATION

This application is a continuation of U.S. application Ser. No. 13/457,280, filed on Apr. 26, 2012, which is a continuation-in-part of U.S. application Ser. No. 13/094,588, filed on Apr. 26, 2011, now issued as U.S. Pat. No. 8,686,200, and U.S. application Ser. No. 13/292,914, filed on Nov. 9, 2011, the entire contents and disclosures of which are incorporated herein by reference.

FIELD OF THE INVENTION

The present invention relates generally to processes for producing alcohol and, in particular, to a process for recovering ethanol with reduced water.

BACKGROUND OF THE INVENTION

Ethanol for industrial use is conventionally produced from organic feed stocks, such as petroleum oil, natural gas, or coal, from feed stock intermediates, such as syngas, or from starchy materials or cellulosic materials, such as corn or sugar cane. Conventional methods for producing ethanol from organic feed stocks, as well as from cellulosic materials, include the acid-catalyzed hydration of ethylene, methanol homologation, direct alcohol synthesis, and Fischer-Tropsch synthesis. Instability in organic feed stock prices contributes to fluctuations in the cost of conventionally produced ethanol, making the need for alternative sources of ethanol production all the greater when feed stock prices rise. Starchy materials, as well as cellulosic materials, are converted to ethanol by fermentation. However, fermentation is typically used for consumer production of ethanol, which is suitable for fuels or human consumption. In addition, fermentation of starchy or cellulosic materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acids, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition, when conversion is incomplete, acid remains in the crude ethanol product, which must be removed to recover ethanol.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol stream and a stream of acetic acid and ethyl acetate, which is recycled to the hydrogenation reactor.

U.S. Pat. No. 7,842,844 describes a process for improving selectivity and catalyst activity and operating life for the conversion of hydrocarbons to ethanol and optionally acetic acid in the presence of a particulate catalyst, said conversion proceeding via a syngas generation intermediate step.

The need remains for improved processes for recovering ethanol from a crude product obtained by reducing alkanoic acids, such as acetic acid, and/or other carbonyl group-containing compounds.

SUMMARY OF THE INVENTION

In a first embodiment, the present invention is directed to a process for producing ethanol, comprising hydrogenating acetic acid in a reactor in the presence of a catalyst to form a crude ethanol product, separating a portion of the crude ethanol product in a first distillation column to yield a first distillate comprising acetaldehyde and ethyl acetate, and a first residue comprising ethanol, acetic acid, ethyl acetate and water, separating a portion of the first residue in a second distillation column to yield a second residue comprising acetic acid and an overhead vapor comprising ethanol, ethyl acetate and water, removing water from at least a portion of the overhead vapor, preferably at least 50% of the overhead vapor, to yield an ethanol mixture stream having a lower water content than the at least a portion of the overhead vapor, and separating at least a portion of the ethanol mixture stream in a third distillation column to yield a third distillate comprising ethyl acetate and a third residue comprising ethanol and less than 8 wt. % water, e.g., less than 3 wt. % water or less than 0.5 wt. % water. In one embodiment, water is removed from the overhead vapor using a water separator selected from the group consisting of an adsorption unit, membrane, extractive column distillation, molecular sieves, and combinations thereof.

In a second embodiment, the present invention is directed to a process for producing ethanol, comprising hydrogenating acetic acid in a reactor in the presence of a catalyst to form a crude ethanol product, separating a portion of the crude ethanol product in a first distillation column to yield a first distillate comprising acetaldehyde and ethyl acetate, and a first residue comprising ethanol, acetic acid, and water, separating a portion of the first residue in a second distillation column to yield a second residue comprising acetic acid and water, and an overhead vapor comprising ethanol and water, wherein a weight majority of the water fed to the second column is removed in the second residue, and removing water from at least a portion of the overhead vapor to yield an ethanol product having less than 8 wt. % water, e.g., less than 3 wt. % water or less than 0.5 wt. % water.

In a third embodiment, the present invention is directed to a process for producing ethanol, comprising providing a crude ethanol product, separating a portion of the crude ethanol product in a first distillation column to yield a first distillate comprising acetaldehyde and ethyl acetate, and a first residue comprising ethanol, acetic acid, ethyl acetate and water, separating a portion of the first residue in a second distillation column to yield a second residue comprising acetic acid and an overhead vapor comprising ethanol, ethyl acetate and water, removing water from at least a portion of the overhead vapor, preferably at least 50% of the overhead vapor, to yield an ethanol mixture stream having a lower water content than the at least a portion of the overhead vapor, and separating at least a portion of the ethanol mixture stream in a third distillation column to yield a third distillate comprising ethyl acetate and a third residue comprising ethanol and less than 8 wt. % water, e.g., less than 3 wt. % water or less than 0.5 wt. % water. In one embodiment, water is removed from the overhead vapor using a water separator selected from the group consisting of an adsorption unit, membrane, extractive column distillation, molecular sieves, and combinations thereof.

BRIEF DESCRIPTION OF DRAWINGS

The invention may be more completely understood in consideration of the following detailed description of various embodiments of the invention in connection with the accompanying drawings, wherein like numerals designate similar parts.

DETAILED DESCRIPTION OF THE INVENTION

Figure 1:
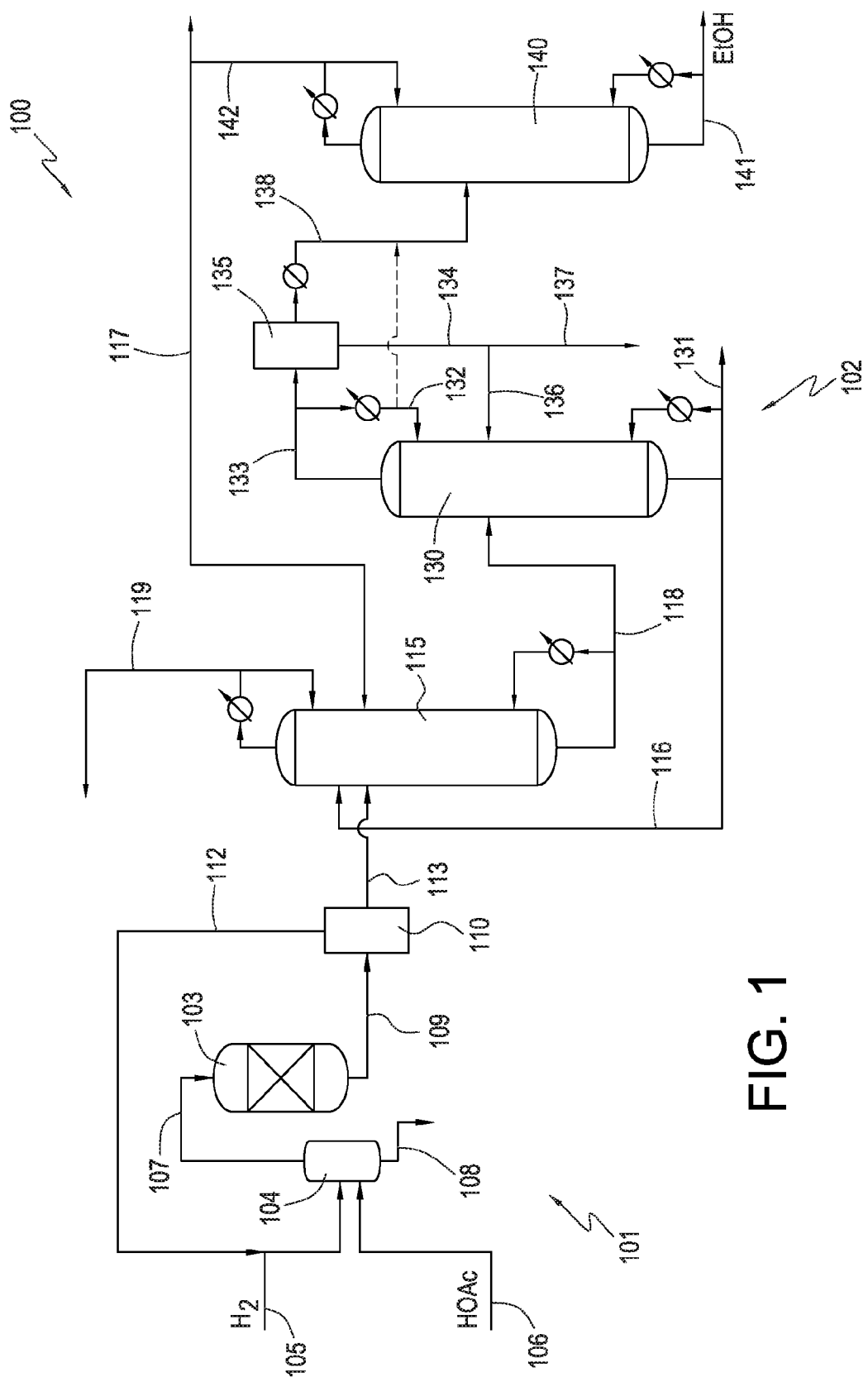
FIG. 1 is a schematic diagram of an ethanol production system with multiple distillation columns to recover ethanol including an acid column and water separator in accordance with one embodiment of the present invention.

The present invention relates to processes for recovering ethanol produced by hydrogenating acetic acid in the presence of a catalyst. The hydrogenation reaction produces a crude ethanol product that comprises ethanol, water, ethyl acetate, acetaldehyde, acetic acid, and other impurities. Water is co-produced with ethanol in the hydrogenation reaction in about a 1:1 molar ratio, and thus producing ethanol also results in the production of water. This makes recovering industrial grade ethanol or fuel grade ethanol difficult due to the excess water. In some embodiments, the processes of the present invention involve separating the crude ethanol product in a first column into a residue stream comprising ethanol, water, ethyl acetate and/or acetic acid and a distillate stream comprising acetaldehyde and ethyl acetate. The first column primarily removes light organics in the distillate and returns those organics to the reactor for subsequent hydrogenation. Subsequently, the ethanol is removed from the residue stream to yield an ethanol product. Advantageously, this separation approach results in reducing energy requirements to recover ethanol, in particular anhydrous ethanol for fuel grade ethanol, from the crude ethanol product.

In recovering ethanol, the processes of the present invention use one or more distillation columns. In preferred embodiments, the residue stream from in the initial column, e.g., first column, comprises a substantial portion of the ethanol, water and acetic acid from the crude ethanol product. The residue stream, for example, may comprise at least 50% of the ethanol from the crude ethanol product, and more preferably at least 70%. In terms of ranges, the residue stream may comprise from 50% to 99.9% of the ethanol from the crude ethanol product, and more preferably from 70% to 99%. Preferably, the amount of ethanol from the crude ethanol product recovered in the residue may be greater than 97.5%, e.g. greater than 99%.

Depending on the ethyl acetate concentration in the residue and whether in situ esterification occurs in the residue or in an esterification reactor, it may be necessary to further separate the ethyl acetate and ethanol in a separate column. Preferably, this separate column is located after the water has been removed using a distillation column and water separator. Generally, a separate column may be necessary when the residue comprises at least 50 wppm ethyl acetate or esterification would be expected to occur. When the residue comprises less than 50 wppm ethyl acetate, it may not be necessary to use a separate column to separate ethyl acetate and ethanol.

In preferred embodiments, the residue stream comprises a substantial portion of the water and acetic acid from the crude ethanol product. The residue stream may comprise at least 80% of the water from the crude ethanol product, and more preferably at least 90%. In terms of ranges, the residue stream preferably comprises from 80% to 100% of the water from the crude ethanol product, and more preferably from 90% to 99.4%. The residue stream may comprise at least 85% of the acetic acid from the crude ethanol product, e.g., at least 90% and more preferably about 100%. In terms of ranges, the residue stream preferably comprises from 85% to 100% of the acetic acid from the crude ethanol product, and more preferably from 90% to 100%. In one embodiment, substantially all of the acetic acid is recovered in the residue stream.

The residue stream, which comprises ethanol, ethyl acetate, water, and acetic acid, may be further separated to recover ethanol. Because these compounds may not be in equilibrium, additional ethyl acetate may be produced through esterification of ethanol and acetic acid. In one preferred embodiment, the water and acetic acid may be removed as another residue stream in a separate distillation column. In addition, the water carried over in the separate distillation column may be removed with a water separator that is selected from the group consisting of an adsorption unit, membrane, extractive column distillation, molecular sieves, or a combination thereof.

In one embodiment each of the columns is sized to be capital and economically feasible for the rate of ethanol production. The total diameter for the columns used to separate the crude ethanol product may be from 5 to 40 meters, e.g., from 10 to 30 meters or from 12 to 20 meters. Each column may have a varying size. In one embodiment, the ratio of column diameter in meters for all the distillation columns to tons of ethanol produced per hour is from 1:2 to 1:30, e.g., from 1:3 to 1:20 or from 1:4 to 1:10. This would allow the process to achieve production rates of 25 to 250 tons of ethanol per hour.

The distillate from the initial column comprises light organics, such as acetaldehyde, diethyl acetal, acetone, and ethyl acetate. As a result, the initial column provides an efficient means for removing acetaldehyde and ethyl acetate. In addition, minor amounts of ethanol and water may be present in the distillate. In addition, acetaldehyde, diethyl acetal, and acetone are not carried over with the ethanol when multiple columns are used, thus reducing the formation of byproducts from acetaldehyde, diethyl acetal, and acetone. In particular, acetaldehyde and/or ethyl acetate may be returned to the reactor and converted to additional ethanol. In another embodiment, a purge may remove these light organics from the system.

In one embodiment, the residue from the initial column comprises ethyl acetate. Although ethyl acetate is also partially withdrawn into the first distillate, a higher ethyl acetate concentration in the first residue advantageously leads to increased ethanol concentration in the first residue and decreased ethanol concentrations in the first distillate. Thus overall ethanol recovery may be increased. Ethyl acetate may be separated from ethanol in a separate column near the end of the purification process. In removing ethyl acetate, additional light organics may also be removed and thus improve the quality of the ethanol product by decreasing impurities. Preferably, water and/or acetic acid may be removed prior to the ethyl acetate/ethanol separation.

In one embodiment, after the ethyl acetate is separated from ethanol downstream of the initial column, the ethyl acetate is returned to the initial column and fed near the top of that column. This allows for any ethanol removed with the ethyl acetate to be recovered and further reduces the amount of ethanol being recycled to the reactor. Decreasing the amount of ethanol recycled to the reactor may reduce reactor capital and improve efficiency in recovering ethanol. Preferably, the ethyl acetate is removed in the distillate of the first column and returned to the reactor with the acetaldehyde.

The processes of the present invention may be used with any hydrogenation process for producing ethanol. The materials, catalysts, reaction conditions, and separation processes that may be used in the hydrogenation of acetic acid are described further below.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethane oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from other carbon sources have drawn increasing interest. In particular, when petroleum is relatively expensive, it may become advantageous to produce acetic acid from synthesis gas ("syngas") that is derived from other available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from a variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Biomass-derived syngas has a detectable $^{14}C$ isotope content as compared to fossil fuels such as coal or natural gas. An equilibrium forms in the Earth's atmosphere between constant new formation and constant degradation, and so the proportion of the $^{14}C$ nuclei in the carbon in the atmosphere on Earth is constant over long periods. The same distribution ratio $n^{14}C:n^{12}C$ ratio is established in living organisms as is present in the surrounding atmosphere, which stops at death and $^{14}C$ decomposes at a half life of about 6000 years. Methanol, acetic acid and/or ethanol formed from biomass-derived syngas would be expected to have a $^{14}C$ content that is substantially similar to living organisms. For example, the $^{14}C$:$^{12}C$ ratio of the methanol, acetic acid and/or ethanol may be from one half to about 1 of the $^{14}C$:$^{12}C$ ratio for living organisms. In other embodiments, the syngas, methanol, acetic acid and/or ethanol described herein are derived wholly from fossil fuels, i.e. carbon sources produced over 60,000 years ago, may have no detectable $^{14}C$ content.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally, in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. No. 6,509,180, and U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. Another biomass source is black liquor, which is an aqueous solution of lignin residues, hemicellulose, and inorganic chemicals.

U.S. Pat. No. RE 35,377, also incorporated herein by reference, provides a method for the production of methanol by converting carbonaceous materials such as oil, coal, natural gas and biomass materials. The process includes hydrogasification of solid and/or liquid carbonaceous materials to obtain a process gas which is steam pyrolized with additional natural gas to form syngas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

Acetic acid fed to the hydrogenation reactor may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid, or propanal, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The reactor pressure may range from 100 kPa to 4500 kPa, e.g., from 150 kPa to 3500 kPa, or from 500 kPa to 3000 kPa. The reactants may be fed to the reactor at a gas hourly space velocity (GHSV) from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 18:1 to 2:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, from 0.1 to 100 seconds.

The hydrogenation of acetic acid to form ethanol is preferably conducted in the presence of a hydrogenation catalyst. Exemplary catalysts are further described in U.S. Pat. Nos. 7,608,744 and 7,863,489, and U.S. Pub. Nos. 2010/0121114 and 2010/0197985, the entireties of which are incorporated herein by reference. In another embodiment, the catalyst comprises a Co/Mo/S catalyst of the type described in U.S. Pub. No. 2009/0069609, the entirety of which is incorporated herein by reference. In some embodiments, the catalyst may be a bulk catalyst.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel.

In certain embodiments where the catalyst includes two or more metals, e.g., a first metal and a second metal, the first metal preferably is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 7.5 wt. %.

Preferred metal combinations for exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ ruthenium, cobalt/tin, silver/palladium, copper/palladium, copper/zinc, nickel/palladium, gold/palladium, ruthenium/rhenium, or ruthenium/iron.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. When present, the total weight of the third metal preferably is from 0.05 to 20 wt. %, e.g., from 0.1 to 10 wt. %, or from 0.1 to 7.5 wt. %. In one embodiment, the catalyst may comprise platinum, tin and cobalt.

In addition to one or more metals, in some embodiments of the present invention the catalysts further comprise a support or a modified support. As used herein, the term "modified support" refers to a support that includes a support material and a support modifier, which adjusts the acidity of the support material. The total weight of the support or modified support, based on the total weight of the catalyst, preferably is from 75 to 99.9 wt. %, e.g., from 78 to 99 wt. %, or from 80 to 97.5 wt. %. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

The support may be a modified support and the support modifier is present in an amount from 0.1 to 50 wt. %, e.g., from 0.2 to 25 wt. %, from 1 to 20 wt. %, or from 3 to 15 wt. %, based on the total weight of the catalyst. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, $Sb_2O_3$, $WO_3$, $MoO_3$, $Fe_2O_3$, $Cr_2O_3$, $V_2O_5$, $MnO_2$, $CuO$, $Co_2O_3$, and $Bi_2O_3$. Preferred support modifiers include oxides of tungsten, molybdenum, and vanadium.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. The basic support modifier may be selected from the group consisting of oxides and metasilicates of any of sodium, potassium, magnesium, calcium, scandium, yttrium, and zinc, as well as mixtures of any of the foregoing. In one embodiment, the basic support modifier is a calcium silicate, such as calcium metasilicate ($CaSiO_3$). The calcium metasilicate may be crystalline or amorphous.

Catalysts on a modified support may include one or more metals selected from the group consisting of platinum, palladium, cobalt, tin, and rhenium on a silica support, optionally modified by one or more modifiers selected from the group consisting of calcium metasilicate, and one or more oxides of tungsten, molybdenum, and/or vanadium.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

After the washing, drying and calcining of the catalyst is completed, the catalyst may be reduced in order to activate it. Reduction is carried out in the presence of a reducing gas, preferably hydrogen. The reducing gas is optionally continuously passed over the catalyst at an initial ambient temperature that is increased up to 400° C. In one embodiment, the reduction is carried out after the catalyst has been loaded into the reaction vessel where the hydrogenation will be carried out.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a percentage based on acetic acid in the feed. The conversion may be at least 40%, e.g., at least 50%, at least 60%, at least 70% or at least 80%. Although catalysts that have high conversions are desirable, such as at least 80% or at least 90%, in some embodiments a low conversion may be acceptable at high selectivity for ethanol. Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethanol is at least 60%, e.g., at least 70%, or at least 80%. Preferred embodiments of the hydrogenation process also have low selectivity to undesirable products, such as methane, ethane, and carbon dioxide. The selectivity to these undesirable products preferably is less than 4%, e.g., less than 2% or less than 1%.

The term "productivity," as used herein, refers to the grams of a specified product, e.g., ethanol, formed during the hydrogenation based on the kilograms of catalyst used per hour. The productivity may range from 100 to 3,000 grams of ethanol per kilogram of catalyst per hour.

In various embodiments of the present invention, the crude ethanol product produced by the hydrogenation process, before any subsequent processing, such as purification and separation, will typically comprise acetic acid, ethanol and water. Exemplary compositional ranges for the crude ethanol product are provided in Table 1, excluding hydrogen. The "others" identified in Table 1 may include, for example, esters, ethers, aldehydes, ketones, alkanes, and carbon dioxide.

TABLE 1

| CRUDE ETHANOL PRODUCT COMPOSITIONS | | | | |
|---|---|---|---|---|
| Component | Conc. (wt. %) | Conc. (wt. %) | Conc. (wt. %) | Conc. (wt. %) |
| Ethanol | 5 to 72 | 15 to 72 | 15 to 70 | 25 to 65 |
| Acetic Acid | 0 to 90 | 0 to 50 | 0 to 35 | 0 to 15 |
| Water | 5 to 40 | 5 to 30 | 10 to 30 | 10 to 26 |
| Ethyl Acetate | 0 to 30 | 1 to 25 | 3 to 20 | 5 to 18 |
| Acetaldehyde | 0 to 10 | 0 to 3 | 0.1 to 3 | 0.2 to 2 |
| Others | 0.1 to 10 | 0.1 to 6 | 0.1 to 4 | — |

At higher conversions, the crude ethanol product of Table 1 may have low concentrations of acetic acid. The crude ethanol product may comprise acetic acid, for example, in an amount ranging from 0.01 wt. % to 20 wt. %, e.g., 0.05 wt. % to 15 wt. %, from 0.1 wt. % to 10 wt. % or from 1 wt. % to 5 wt. %. In embodiments having lower amounts of acetic acid, the conversion of acetic acid is preferably greater than 75%, e.g., greater than 85% or greater than 90%. In addition, the selectivity to ethanol may also be preferably high, and is preferably greater than 75%, e.g., greater than 85% or greater than 90%.

Exemplary ethanol recovery systems in accordance with embodiments of the present invention are shown in FIGS. 1-5. Each hydrogenation system 100 provides a suitable hydrogenation reactor and a process for separating ethanol from the crude reaction mixture according to an embodiment of the invention. System 100 comprises reaction zone 101 and separation zone 102. Further modifications and additional components to reaction zone 101 and separation zone 102 are described below.

As shown in FIGS. 1-5, the feed to reactor 103 comprises fresh acetic acid. Hydrogen and acetic acid are fed to vaporizer 104 via lines 105 and 106, respectively, to create a vapor feed stream in line 107 that is directed to reactor 103. In one embodiment, lines 105 and 106 may be combined and jointly fed to the vaporizer 104. The temperature of the vapor feed stream in line 107 is preferably from 100° C. to 350° C., e.g., from 120° C. to 310° C. or from 150° C. to 300° C. Any feed that is not vaporized is removed from vaporizer 104, via blowdown 108. In addition, although line 107 is shown as being directed to the top of reactor 103, line 107 may be directed to the side, upper portion, or bottom of reactor 103.

Reactor 103 contains the catalyst that is used in the hydrogenation of the carboxylic acid, preferably acetic acid. In one embodiment, one or more guard beds (not shown) may be used upstream of the reactor, optionally upstream of vaporizer 104, to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens. During the hydrogenation process, a crude ethanol product is withdrawn, preferably continuously, from reactor 103 via line 109.

The crude ethanol product may be condensed and fed to a separator 110, which, in turn, forms a vapor stream 112 and a liquid stream 113. In some embodiments, separator 110 may comprise a flasher or a knockout pot. The separator 110 may operate at a temperature from 20° C. to 350° C., e.g., from 30° C. to 325° C. or from 60° C. to 250° C. The pressure of separator 110 may be from 100 kPa to 3000 kPa, e.g., from 125 kPa to 2500 kPa or from 150 kPa to 2200 kPa. Optionally, the crude ethanol product in line 109 may pass through one or more membranes to separate hydrogen and/or other non-condensable gases.

Vapor stream 112 exiting separator 110 may comprise hydrogen and hydrocarbons, and may be purged and/or returned to reaction zone 101. As shown, vapor stream 112 is combined with the hydrogen feed 105 and co-fed to vaporizer 104. In some embodiments, the returned vapor stream 112 may be compressed before being combined with hydrogen feed 105.

Liquid stream 113 from separator 110 is withdrawn and directed as a feed composition to the side of first distillation column 115, also referred to as an "extractive column." Liquid stream 113 may be heated from ambient temperature to a temperature of up to 70° C., e.g., up to 50° C., or up to 40° C. The additional energy required to pre-heat liquid stream 113 above 70° C. does not achieve the desired energy efficiency in first column 115 with respect to reboiler duties.

In another embodiment, liquid stream 113 is not separately preheated, but is withdrawn from separator 110, and cooled if needed, at a temperature of less than 70° C., e.g., less than 50° C., or less than 40° C., and directly fed to first column 115.

In one embodiment, the contents of liquid stream 113 are substantially similar to the crude ethanol product obtained from the reactor, except that the composition has been depleted of hydrogen, carbon dioxide, methane and/or ethane, which have been removed by separator 110. Accordingly, liquid stream 113 may also be referred to as a crude ethanol product. Exemplary components of liquid stream 113 are provided in Table 2. It should be understood that liquid stream 113 may contain other components, not listed in Table 2.

TABLE 2

FEED COMPOSITION TO COLUMN 115
(Liquid Stream 113)

|  | Conc. (wt. %) | Conc. (wt. %) | Conc. (wt. %) |
|---|---|---|---|
| Ethanol | 5 to 72 | 10 to 70 | 15 to 65 |
| Acetic Acid | <90 | 5 to 80 | 0 to 35 |
| Water | 5 to 40 | 5 to 30 | 10 to 26 |
| Ethyl Acetate | <30 | 1 to 25 | 3 to 20 |
| Acetaldehyde | <10 | 0.001 to 3 | 0.1 to 3 |
| Acetal | <5 | 0.01 to 5 | 0.01 to 3 |
| Acetone | <5 | 0.0005 to 0.05 | 0.001 to 0.03 |

The amounts indicated as less than (<) in the tables throughout the present specification are preferably not present and if present may be present in amounts greater than 0.0001 wt. %.

In one embodiment, the ethyl acetate concentration in the liquid stream 113 may affect the first column reboiler duty and size. Decreasing ethyl acetate concentrations may allow for reduced reboiler duty and size. In one embodiment, to reduce the ethyl acetate concentration (a) the catalyst in reactor may convert ethyl acetate in addition to acetic acid; (b) the catalyst may be less selective for ethyl acetate, and/or (c) the feed to reactor, including recycles, may contain less ethyl acetate.

In the embodiment shown in FIG. 1, liquid stream 113 is introduced in the upper part of first column 115, e.g., upper half or upper third. In addition to liquid stream 113, an extractive agent 116 and an ethyl acetate recycle stream 117 are also fed to first column. Extractive agent 116 is preferably introduced above liquid stream 113. Extractive agent 116 may be heated from ambient temperature to a temperature of up to 70° C., e.g., up to 50° C., or up to 40° C. In another embodiment, Extractive agent 116 is not separately preheated, but is withdrawn from second column 130, and cooled, if necessary, to a temperature of less than 70° C., e.g., less than 50° C., or less than 40° C., and directly fed to first column 115. Depending on the ethyl acetate concentration of ethyl acetate recycle stream 117 this stream may be introduced above or near the feed point of the liquid stream 113. Depending on the targeted ethyl acetate concentration in the distillate of first column 115 the feed point of ethyl acetate recycle stream 117 will vary.

Liquid stream 113 and ethyl acetate recycle stream 117 collectively comprise the organic feed to first column 115. In one embodiment, the organic feed comprises from 1 to 25% of ethyl acetate recycle stream 117, e.g., from 3% to 20% or from 5% to 15%, the remainder being supplied by liquid stream 113. This amount may vary depending on the production of reactor 103 and the amount of ethyl acetate to be recycled.

Extractive agent 116 preferably comprises water that has been retained within the system. As described herein, extractive agent 116 may be obtained from a portion of the second residue. Extractive agent 116 may be a dilute acid stream comprising up to 20 wt. % acetic acid, e.g., up to 10 wt. % acetic acid or up to 5 wt. % acetic acid. In one embodiment, the mass flow ratio of water in extractive agent 116 to the mass flow of the organic feed, which comprises liquid stream 113 and ethyl acetate recycle stream 117, may range from 0.05:1 to 2:1, e.g., from 0.07 to 0.9:1 or from 0.1:1 to 0.7:1. It is preferred that the mass flow of extractive agent 116 is less than the mass flow of the organic feed.

In one embodiment, first column 115 is a tray column having from 5 to 90 theoretical trays, e.g., from 10 to 60 theoretical trays or from 15 to 50 theoretical trays. The number of actual trays for each column may vary depending on the tray efficiency, which is typically from 0.5 to 0.7 depending on the type of tray. The trays may be sieve trays, fixed valve trays, movable valve trays, or any other suitable design known in the art. In other embodiments, a packed column having structured packing or random packing may be employed.

When first column 115 is operated under 50 kPa, the temperature of the residue exiting in line 118 preferably is from 20° C. to 100° C., e.g., from 30° C. to 90° C. or from 40° C. to 80° C. The base of column 115 may be maintained at a relatively low temperature by withdrawing a residue stream comprising ethanol, ethyl acetate, water, and acetic acid, thereby providing an energy efficiency advantage. The temperature of the distillate exiting in line 119 from column 115 preferably at 50 kPa is from 10° C. to 80° C., e.g., from 20° C. to 70° C. or from 30° C. to 60° C. The pressure of first column 115 may range from 0.1 kPa to 510 kPa, e.g., from 1 kPa to 475 kPa or from 1 kPa to 375 kPa. In some embodiments, first column 115 may operate under a vacuum of less than 70 kPa, e.g., less than 50 kPa, or less than 20 kPa. Operating under a vacuum may decrease the reboiler duty and reflux ratio of first column 115. However, a decrease in operating pressure for first column 115 does not substantially affect column diameter.

In first column 115, a weight majority of the ethanol, water, acetic acid, are removed from the organic feed, including liquid stream 113 and ethyl acetate recycle stream 117, and are withdrawn, preferably continuously, as residue in line 118. This includes any water added as an extractive agent 116. Concentrating the ethanol in the residue reduces the amount of ethanol that is recycled to reactor 103 and in turn reduces the size of reactor 103. Preferably less than 10% of the ethanol from the organic feed, e.g., less than 5% or less than 1% of the ethanol, is returned to reactor 103 from first column 115. In addition, concentrating the ethanol also will concentrate the water and/or acetic acid in the residue. In one embodiment, at least 90% of the ethanol from the organic feed is withdrawn in the residue, and more preferably at least 95%. In addition, ethyl acetate may also be present in the first residue in line 118. The reboiler duty may decrease with an ethyl acetate concentration increase in the first residue in line 118.

First column 115 also forms a distillate in line 119 that may be condensed and refluxed, for example, at a ratio from 30:1 to 1:30, e.g., from 10:1 to 1:10 or from 5:1 to 1:5. Higher mass flow ratios of water to organic feed may allow first column 115 to operate with a reduced reflux ratio.

The first distillate in line 119 preferably comprises a weight majority of the acetaldehyde and ethyl acetate from liquid stream 113, as well as from ethyl acetate recycle stream 117. In one embodiment, the first distillate in line 119 comprises a concentration of ethyl acetate that is less than the ethyl acetate concentration for the azeotrope of ethyl acetate and water, and more preferably less than 75 wt. %.

Figure 2:
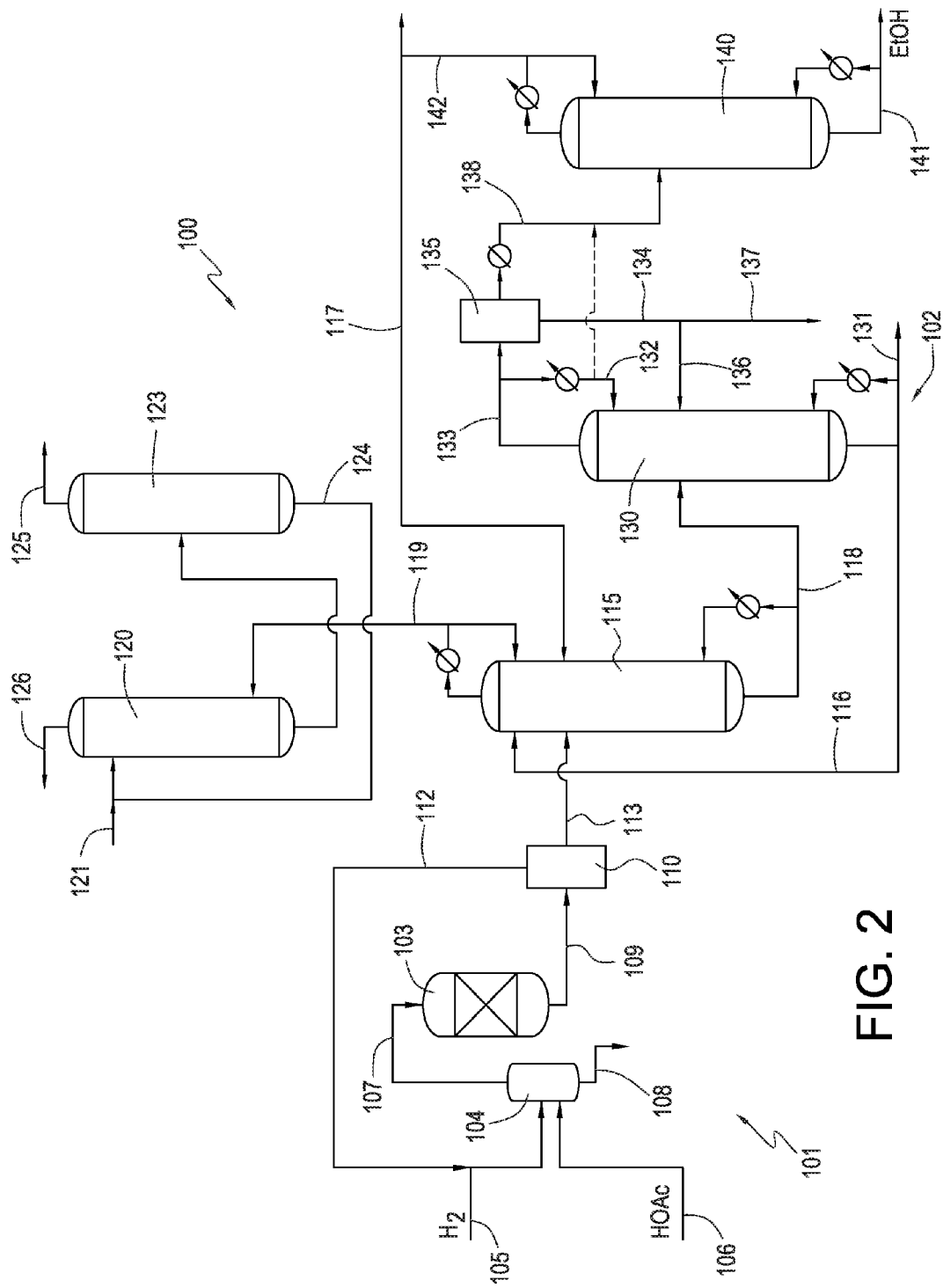
FIG. 2 is a schematic diagram of an ethanol production system with multiple distillation columns having an extractive distillation for recovering ethanol from a stream being recycled to the reactor in accordance with one embodiment of the present invention.

In some embodiments, first distillate in stream 119 also comprises ethanol. Returning the ethanol may require an increase in reactor capacity to maintain the same level of ethanol efficiency. To recover ethanol, the first distillate in line 119 may be fed, as is shown in FIG. 2, to an extraction column 120 to recover ethanol and reduce the amount of ethanol that is recycled to reactor 103. Extraction column 120 may be a multi-stage extractor. As shown, the first distillate in line 119 at least one extractant 121 are fed to extraction column 120. In one embodiment, extractant 121 may comprise one or more of benzene, propylene glycol, or cyclohexane. Although water may be used, the extractant 121 preferably does not form an azeotrope with ethanol. Preferably, the extractant extracts ethanol from the first distillate in extract 122. The extractant may be recovered from extract 122 in recovery column 123 and returned via line 124. The ethanol stream in line 125 may be combined with the ethanol product or returned to one of the distillation columns, such as first column 115. The raffinate 126 may be returned to reaction zone 101. Preferably, raffinate 126, which comprises acetaldehyde and ethyl acetate, is deficient in ethanol with respect to first distillate in line 119.

Exemplary components of the distillate and residue compositions for first column 115 are provided in Table 3 below. It should also be understood that the distillate and residue may also contain other components, not listed in Table 3. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

EXTRACTIVE COLUMN

|  | Conc. (wt. %) | Conc. (wt. %) | Conc. (wt. %) |
|---|---|---|---|
| Distillate |  |  |  |
| Ethyl Acetate | 10 to 85 | 15 to 80 | 20 to 75 |
| Acetaldehyde | 0.1 to 70 | 0.2 to 65 | 0.5 to 65 |
| Acetal | <3 | 0.01 to 2 | 0.05 to 1.5 |
| Acetone | <0.05 | 0.001 to 0.03 | 0.01 to 0.025 |
| Ethanol | <25 | 0.001 to 20 | 0.01 to 15 |
| Water | 0.1 to 20 | 1 to 15 | 2 to 10 |
| Acetic Acid | <2 | <0.1 | <0.05 |
| Residue |  |  |  |
| Acetic Acid | 0.1 to 50 | 0.5 to 40 | 1 to 30 |
| Water | 20 to 85 | 25 to 80 | 30 to 75 |
| Ethanol | 10 to 75 | 15 to 70 | 20 to 65 |
| Ethyl Acetate | 0.005 to 30 | 0.03 to 25 | 0.08 to 1 |

In one embodiment of the present invention, first column 115 may be operated at a temperature where most of the water, ethanol, and acetic acid are removed into the residue stream and only a small amount of ethanol and water is collected in the distillate stream due to the formation of binary and tertiary azeotropes. The weight ratio of water in the residue in line 118 to water in the distillate in line 119 may be greater than 1:1, e.g., greater than 2:1. The weight ratio of ethanol in the residue to ethanol in the distillate may be greater than 1:1, e.g., greater than 2:1.

The amount of acetic acid in the first residue may vary depending primarily on the conversion in reactor 103. In one embodiment, when the conversion is high, e.g., greater than 90%, the amount of acetic acid in the first residue may be less than 10 wt. %, e.g., less than 5 wt. % or less than 2 wt. %. In other embodiments, when the conversion is lower, e.g., less than 90%, the amount of acetic acid in the first residue may be greater than 10 wt. %.

The first distillate in line 119 preferably is substantially free of acetic acid, e.g., comprising less than 1000 wppm, less than 500 wppm or less than 100 wppm acetic acid. The distillate may be purged from the system or recycled in whole or part to reactor 103. In some embodiments, when the distillate comprises ethyl acetate and acetaldehyde, the distillate may be further separated, e.g., in a distillation column (not shown), into an acetaldehyde stream and an ethyl acetate stream. The ethyl acetate stream may also be hydrolyzed or reduced with hydrogen, via hydrogenolysis, to produce ethanol. Either of these streams may be returned to reactor 103 or separated from system 100 as additional products.

Some species, such as acetals, may decompose in first column 115 such that very low amounts, or even no detectable amounts, of acetals remain in the distillate or residue.

In addition, an equilibrium reaction between acetic acid/ethanol and ethyl acetate may occur in the crude ethanol product after exiting reactor 103 or first column 115. Without being bound by theory, ethyl acetate may be formed in the reboiler of first column 115. Depending on the concentration of acetic acid in the crude ethanol product, this equilibrium may be driven toward formation of ethyl acetate. This reaction may be regulated through the residence time and/or temperature of the crude ethanol product.

Figure 3:
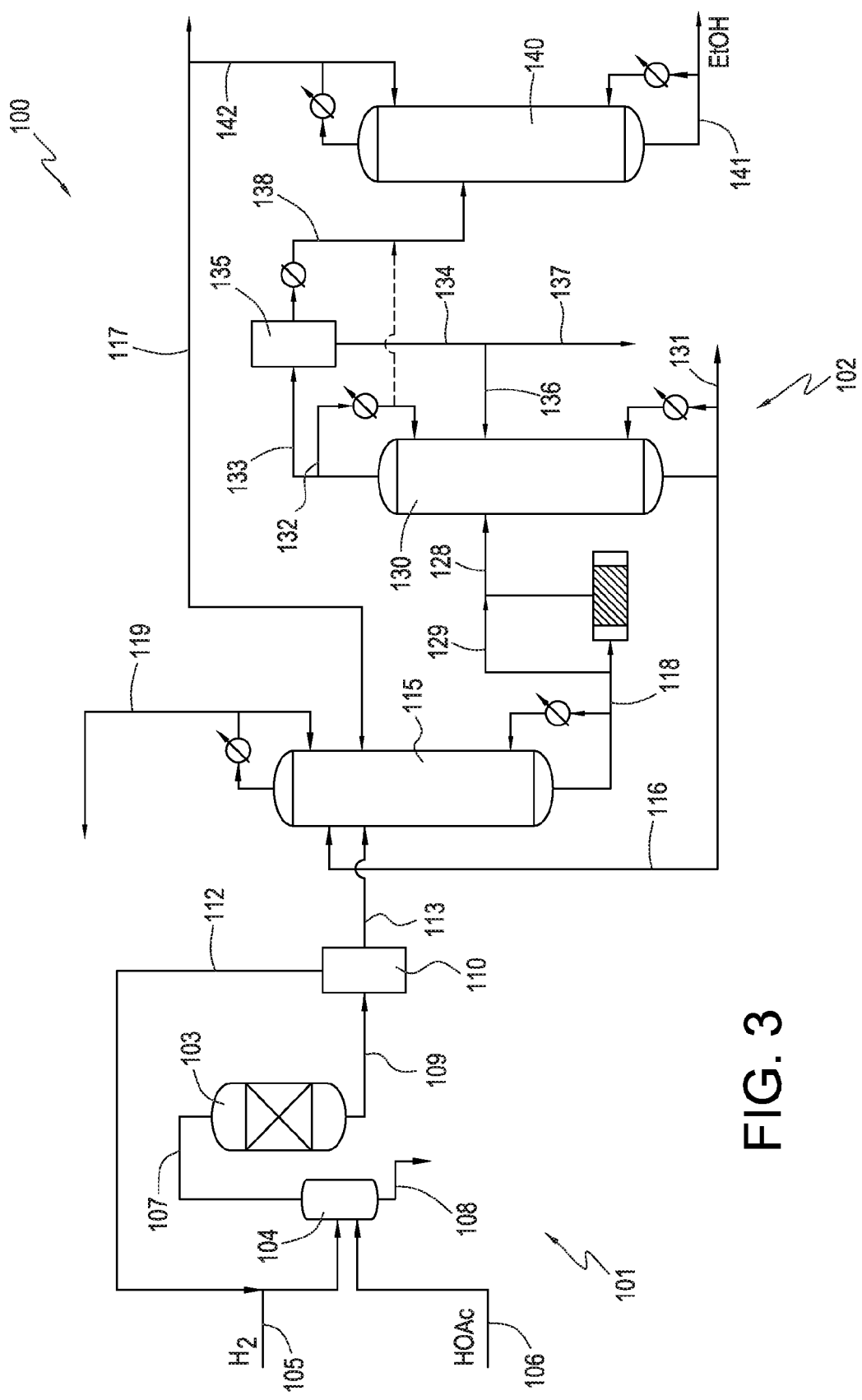
FIG. 3 is a schematic diagram of an ethanol production system with multiple distillation columns to recover ethanol including an acid column and vapor esterification unit in accordance with one embodiment of the present invention.

In one embodiment, due to the composition of first residue in line 118 the equilibrium may favor esterification to produce ethyl acetate. While the esterification, either in the liquid or vapor phase, may consume ethanol, the esterification may also reduce the amount of acetic acid that needs to be removed from the process. Ethyl acetate may be removed from first column 115 or from a second column 130. The esterification may be further promoted by passing a portion of the first residue in line 118 through an esterification reactor 127, as shown in FIG. 3. The esterification reactor may be either a liquid or vapor phase reactor and may comprise an acidic catalyst. A vapor phase reactor is preferred to convert some of the first residue into an intermediate vapor feed 128 to be introduced into the second column 130. Acid-catalyzed esterification reactions may be used with some embodiments of the present invention. The catalyst should be thermally stable at reaction temperatures. Suitable catalysts may be solid acid catalysts comprising an ion exchange resin, zeolites, Lewis acid, metal oxides, inorganic salts and hydrates thereof, heteropoly acids, and salts thereof. Silica gel, aluminum oxide, and aluminum phosphate are also suitable catalysts. Acid catalysts include, but are not limited to, sulfuric acid, and tosic acid. In addition, Lewis acids may also be used as esterification catalysts, such as scandium(III) or lanthanide (III) triflates, hafnium(IV) or zirconium(IV) salts, and diarylammonium arenesulfonates. The catalyst may also include sulfonated (sulphonic acid) ion-exchange resins (e.g., gel-type and macroporous sulfonated styrene-divinyl benzene IERs), sulfonated polysiloxane resins, sulfonated perfluorinated (e.g., sulfonated poly-perfluoroethylene), or sulfonated zirconia.

To recover ethanol, first residue in line 118, or intermediate vapor feed 128 in FIG. 3, may be further separated depending on the concentration of acetic acid and/or ethyl acetate. In most embodiments of the present invention, residue in line 118 is further separated in a second column 130, also referred to as an "acid column." Second column 130 yields a second residue in line 131 comprising acetic acid and/or water, and a vapor overhead in line 133 comprising ethanol and/or ethyl acetate. In one embodiment, a weight majority of the water and/or acetic acid fed to second column 130 is removed in the second residue in line 131, e.g., at least 60% of the water and/or acetic acid is removed as the second residue in line 131 or more preferably at least 80% of the water and/or acetic acid. An acid column may be desirable, for example, when the acetic acid concentration in the first residue is greater 50 wppm, e.g., greater than 0.1 wt. %, 1 wt. %, e.g., greater than 5 wt. %.

In one embodiment, the first residue in line 118 may be preheated prior to being introduced into second column 130. The first residue in line 118 may be heat integrated with either the residue of the second column 130 or vapor overhead of second column 130. In some embodiments, esterification may be carried out in the vapor phase, as shown in FIG. 3, which results in preheating a portion of the first residue in line 118 to form an intermediate vapor feed 128. For purposes of the present invention, when preheating, it is preferred that less than 30 mol. % of the first residue in line 118 is in the vapor phase, e.g., less than 25 mol. % or less than 20 mol. %. Greater vapor phase contents result in increased energy consumption and a significant increase in the size of second column 130. A portion of the first residue in line 129 may by-pass esterification reactor 127 and be combined with the intermediate vapor feed 128 to maintain the necessary vapor mole fraction.

Esterifying the acetic acid in first residue in line 118 increases the ethyl acetate concentration which leads to increases in the size of second column 130 as well increases in reboiler duty. Thus, the conversion of acetic acid may be controlled depending on the initial ethyl acetate concentration withdrawn from the first column. To maintain an efficient separation, the ethyl acetate concentration of the first residue in line 118 as it is fed to second column is preferably less than 1000 wppm, e.g., less than 800 wppm or less than 600 wppm.

Second column 130 concentrates the ethanol from the first residue such that a majority of the ethanol is carried overhead. Thus, the residue of second column 130 may have an ethanol concentration of less than 5 wt. %, e.g. less than 1 wt. % or less than 0.5 wt. %. Lower ethanol concentrations may be achieved without significant increases in reboiler duty or column size. Thus, in some embodiments it is efficient to reduce the ethanol concentration in the residue to less than 50 wppm, or more preferably less than 25 wppm.

In FIG. 1, the first residue in line 118 is introduced to second column 130, preferably in the top part of column 130, e.g., top half or top third. Feeding the first residue in line 118 in a lower portion of second column 130 may unnecessarily increase the energy requirements of second column. Acid column 130 may be a tray column or packed column. In FIG. 1, second column 130 may be a tray column having from 10 to 110 theoretical trays, e.g., from 15 to 95 theoretical trays or from 20 to 75 theoretical trays. Additional trays may be used if necessary to further reduce the ethanol concentration in the residue. In one embodiment, the reboiler duty and column size may be reduced by increasing the number of trays.

Although the temperature and pressure of second column 130 may vary, when at atmospheric pressure the temperature of the second residue in line 131 preferably is from 95° C. to 160° C., e.g., from 100° C. to 150° C. or from 110° C. to 145° C. In one embodiment, first residue in line 118 is preheated to a temperature that is within 20° C. of the temperature of second residue in line 131, e.g., within 15° C. or within 10° C. The temperature of the vapor overhead exiting in line 133 from second column 130 preferably is from 50° C. to 120° C., e.g., from 75° C. to 118° C. or from 80° C. to 115° C. The temperature gradient may be sharper in the base of second column 130.

The pressure of second column 130 may range from 0.1 kPa to 510 kPa, e.g., from 1 kPa to 475 kPa or from 1 kPa to 375 kPa. In one embodiment, second column 130 operates above atmospheric pressure, e.g., above 170 kPa or above 375 kPa. Second column 130 may be constructed of a material such as 316L SS, Allot 2205 or Hastelloy C, depending on the operating pressure. The reboiler duty and column size for the second column remain relatively constant until the ethanol concentration in the vapor overhead in line 133 is greater than 90 wt. %.

As described herein, first column 115 is an extractive column that preferably uses water as the extractive agent. The additional water is preferably separated in second column 130. While using water as an extractive agent may reduce the reboiler duty of first column 115, when the mass flow ratio of water to organic feed is greater than 0.65:1, e.g., greater than 0.6:1 or greater than 0.54:1, the additional water may cause an increase in reboiler duty of second column 130 that offsets any benefit gained by first column 115.

A portion of vapor overhead 133 may be withdrawn as a second distillate in line 132 that is condensed and refluxed, for example, at a ratio from 12:1 to 1:12, e.g., from 10:1 to 1:10 or from 8:1 to 1:8. The vapor overhead in line 133 preferably comprises 85 to 92 wt. % ethanol, e.g., about 87 to 90 wt. % ethanol, with the remaining balance being primarily water and ethyl acetate.

In one embodiment, water may be removed prior to recovering the ethanol product. Vapor overhead in line 133 may comprise less than 15 wt. % water, e.g., less than 10 wt. % water or less than 8 wt. % water. As shown in FIG. 1, vapor overhead 133 may be fed to water separator 135, which may be an adsorption unit, membrane, molecular sieves, extractive column distillation, or a combination thereof. In one embodiment, at least 50% of the vapor overhead is fed to water separator 135, e.g., at least 75% or at least 90%.

Water separator 135 in FIG. 1 may be a pressure swing adsorption (PSA) unit. For purposes of clarity the details of the PSA unit are not shown in the figures. The PSA unit is optionally operated at a temperature from 30° C. to 160° C., e.g., from 80° C. to 140° C., and a pressure from 0.01 kPa to 550 kPa, e.g., from 1 kPa to 150 kPa. The PSA unit may comprise two to five beds. Water separator 135 may remove at least 95% of the water from vapor overhead 133, and more preferably from 95% to 99.99% of the water from vapor overhead 133, into a water stream 134. All or a portion of water stream 134 may be returned to second column 130 in line 136, which may increase the reboiler duty and/or size of second column 130. Additionally or alternatively, all or a portion of water stream 134 may be purged via line 137. The remaining portion of vapor overhead 133 exits the water separator 135 as ethanol mixture stream 138. In one embodiment, ethanol mixture stream 138 comprises more than 92 wt. % ethanol, e.g., more than 95 wt. % or more than 99 wt. %. In one embodiment a portion of water stream 137 may be fed to first column 115 as the extractive agent.

A portion of vapor overhead 132 optionally may be mixed with ethanol mixture stream 138 and co-fed to light ends column 140 as shown by the hashed arrow in FIG. 1. This may be desired if additional water is needed to improve separation in light ends column 140. It should be understood that reflux ratios may vary with the number of stages, feed locations, column efficiency and/or feed composition. Operating with a reflux ratio of greater than 3:1 may be less preferred because more energy may be required to operate second column 130.

Exemplary components for ethanol mixture stream 138 and residue compositions for second column 130 are provided in Table 4 below. It should be understood that the distillate and residue may also contain other components, not listed in Table 4. For example, in optional embodiments, when ethyl acetate is in the feed to reactor 103, second residue in line 131, exemplified in Table 4, may also comprise high boiling point components.

TABLE 4

| ACID COLUMN | | | |
|---|---|---|---|
| | Conc. (wt. %) | Conc. (wt. %) | Conc. (wt. %) |
| Ethanol Mixture Stream | | | |
| Ethanol | 90 to 99.9 | 92 to 99 | 96 to 99 |
| Ethyl Acetate | <10 | 0.001 to 5 | 0.005 to 4 |
| Acetaldehyde | <10 | 0.001 to 5 | 0.005 to 4 |
| Water | <10 | 0.001 to 3 | 0.01 to 1 |
| Acetal | <2 | 0.001 to 1 | 0.005 to 0.5 |
| Second Residue | | | |
| Acetic Acid | 0.1 to 45 | 0.2 to 40 | 0.5 to 35 |
| Water | 45 to 100 | 55 to 99.8 | 65 to 99.5 |
| Ethyl Acetate | <0.1 | 0.0001 to 0.05 | 0.0001 to 0.01 |
| Ethanol | <5 | 0.002 to 1 | 0.005 to 0.5 |

The weight ratio of ethanol in the ethanol mixture stream 138 to ethanol in the second residue in line 131 preferably is at least 35:1. Preferably, ethanol mixture stream 138 is substantially free of acetic acid and may contain, if any, trace amounts of acetic acid.

In one embodiment, ethyl acetate fed to second column 130 may concentrate in the vapor overhead and pass through with ethanol mixture stream 138. Thus, preferably no ethyl acetate is withdrawn in the second residue in line 131. Advantageously, this allows most of the ethyl acetate to be subsequently recovered without having to further process the second residue in line 131.

In optional embodiments, the feed to reactor 103 may comprise acetic acid and/or ethyl acetate. When ethyl acetate is used alone as a feed, the crude ethanol product may comprise substantially no water and/or acetic acid. There may be high boiling point components, such as alcohols having more than 2 carbon atoms, e.g., n-propanol, isopropanol, n-butanol, 2-butanol, and mixtures thereof. High boiling point components refer to compounds having a boiling point that is greater than ethanol. The high boiling point components may be removed in second column 130 in the second residue in line 131.

In one embodiment, due to the presence of ethyl acetate in ethanol mixture stream 138, an additional third column 140 may be used to further purify the ethanol. A third column 140, referred to as a "light ends" column, is used for removing ethyl acetate from ethanol mixture stream 138 and producing an ethanol product in the third residue in line 141. Light ends column 140 may be a tray column or packed column. In FIG. 1, third column 140 may be a tray column having from 5 to 90 theoretical trays, e.g., from 10 to 60 theoretical trays or from 15 to 50 theoretical trays.

The feed location of ethanol mixture stream 138 may vary depending on ethyl acetate concentration, but it is preferred to feed ethanol mixture stream 138 to the upper portion of third column 140. Higher concentrations of ethyl acetate may be fed at a higher location in third column 140. The feed location should avoid the very top trays, near the reflux, to avoid excess reboiler duty requirements for the column and an increase in column size. For example, in a column having 45 actual trays, the feed location should between 10 to 15 trays from the top. Feeding at a point above this may increase the reboiler duty and size of light ends column 140.

Ethanol mixture stream 138 may be fed to third column 140 at a temperature of up to 70° C., e.g., up to 50° C., or up to 40° C. In some embodiments it is not necessary to further preheat ethanol mixture stream 138.

Ethyl acetate may be concentrated in the third distillate in line 142. Due to the relatively lower amounts of ethyl acetate fed to third column 140, the third distillate in line 142 may also comprise substantial amounts of ethanol. To recover the ethanol, the third distillate in line 142 may be fed to the first column as ethyl acetate recycle stream 117. Because this increases the demands on the first and second columns, it is preferred that the concentration of ethanol in the third distillate in line 142 be from 70 to 90 wt. %, e.g., from 72 to 88 wt. %, or from 75 to 85 wt. %.

In other embodiments, a portion of the third distillate in line 142 may be purged from the system in line 143 as a separate product, such as an ethyl acetate solvent.

Figure 4:
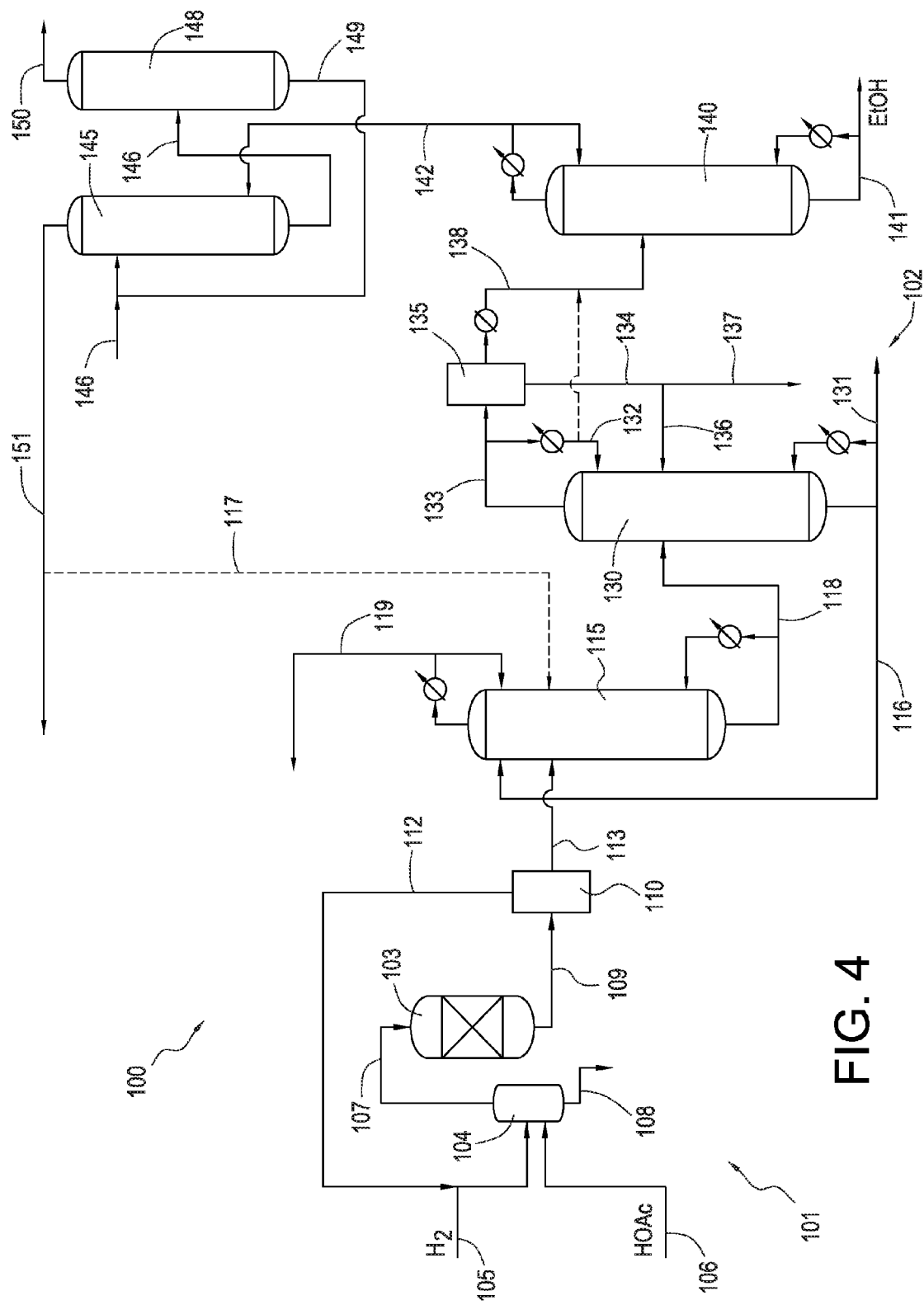
FIG. 4 is a schematic diagram of an ethanol production system with multiple distillation columns having an extractive distillation for recovering ethanol from a stream being recycled to the initial column in accordance with one embodiment of the present invention.

In some embodiments, the ethanol may be recovered using an extractive column 145 as shown in FIG. 4. Extraction column 145 may be a multi-stage extractor. In extraction column 145, the third distillate in line 142 is fed along with at least one extractive agent 146. In one embodiment, the extractive agent may be benzene, propylene glycol, and cyclohexane. Although water may be used, the extractive agent preferably does not form an azeotrope with ethanol. Preferably, the extractive agent extracts ethanol from the third distillate in extract 147. The extractive agent may be recovered in recovery column 148 and returned via line 149. The ethanol stream in line 150 may be combined with the third residue in line 141. The raffinate 151, which comprises ethyl acetate, may be returned to reaction zone 101 or optionally to first column 115 as ethyl acetate recycle stream 117. Preferably, raffinate 151 is deficient in ethanol with respect to third distillate in line 142.

In some embodiment, the third residue in line 141 may comprises less than 8 wt. % water, e.g., less than 3 wt. % water or less than 0.5 wt. % water. In an optional embodiment, the third residue may be further processed to recover ethanol with a desired amount of water, for example, using a further distillation column, adsorption unit, membrane or combination thereof. The reduced water concentration may be less than 3 wt. % water, e.g., less than 0.5 wt. % water or less than 0.1 wt. % water. In most embodiments, the water is removed prior to entering third column 140 using water separator 135 and thus further drying of the ethanol is not required.

Third column 140 is preferably a tray column as described above and preferably operates at atmospheric pressure. The temperature of the third residue in line 141 exiting from third column 140 preferably is from 65° C. to 110° C., e.g., from 70° C. to 100° C. or from 75° C. to 80° C. The temperature of the third distillate in line 142 exiting from third column 140 preferably is from 30° C. to 70° C., e.g., from 40° C. to 65° C. or from 50° C. to 65° C.

The pressure of third column 140 may range from 0.1 kPa to 510 kPa, e.g., from 1 kPa to 475 kPa or from 1 kPa to 375 kPa. In some embodiments, third column 140 may operate under a vacuum of less than 70 kPa, e.g., less than 50 kPa, or less than 20 kPa. Decreasing operating pressure substantially decreases column diameter and reboiler duty for third column 140.

Exemplary components for the ethanol mixture stream and the residue compositions for third column 140 are provided in Table 5 below. It should be understood that the distillate and residue may also contain other components, not listed in Table 5.

TABLE 5

| LIGHT ENDS COLUMN | | | |
|---|---|---|---|
| | Conc. (wt. %) | Conc. (wt. %) | Conc. (wt. %) |
| Third Distillate | | | |
| Ethanol | 70 to 99 | 72 to 95 | 75 to 90 |
| Ethyl Acetate | 1 to 30 | 1 to 25 | 1 to 15 |
| Acetaldehyde | <15 | 0.001 to 10 | 0.1 to 5 |
| Water | <10 | 0.001 to 2 | 0.01 to 1 |
| Acetal | <2 | 0.001 to 1 | 0.01 to 0.5 |
| Third Residue | | | |
| Ethanol | 80 to 99.5 | 85 to 97 | 90 to 95 |
| Water | <8 | 0.001 to 3 | 0.01 to 1 |
| Ethyl Acetate | <1.5 | 0.0001 to 1 | 0.001 to 0.5 |
| Acetic Acid | <0.5 | <0.01 | 0.0001 to 0.01 |

Figure 5:
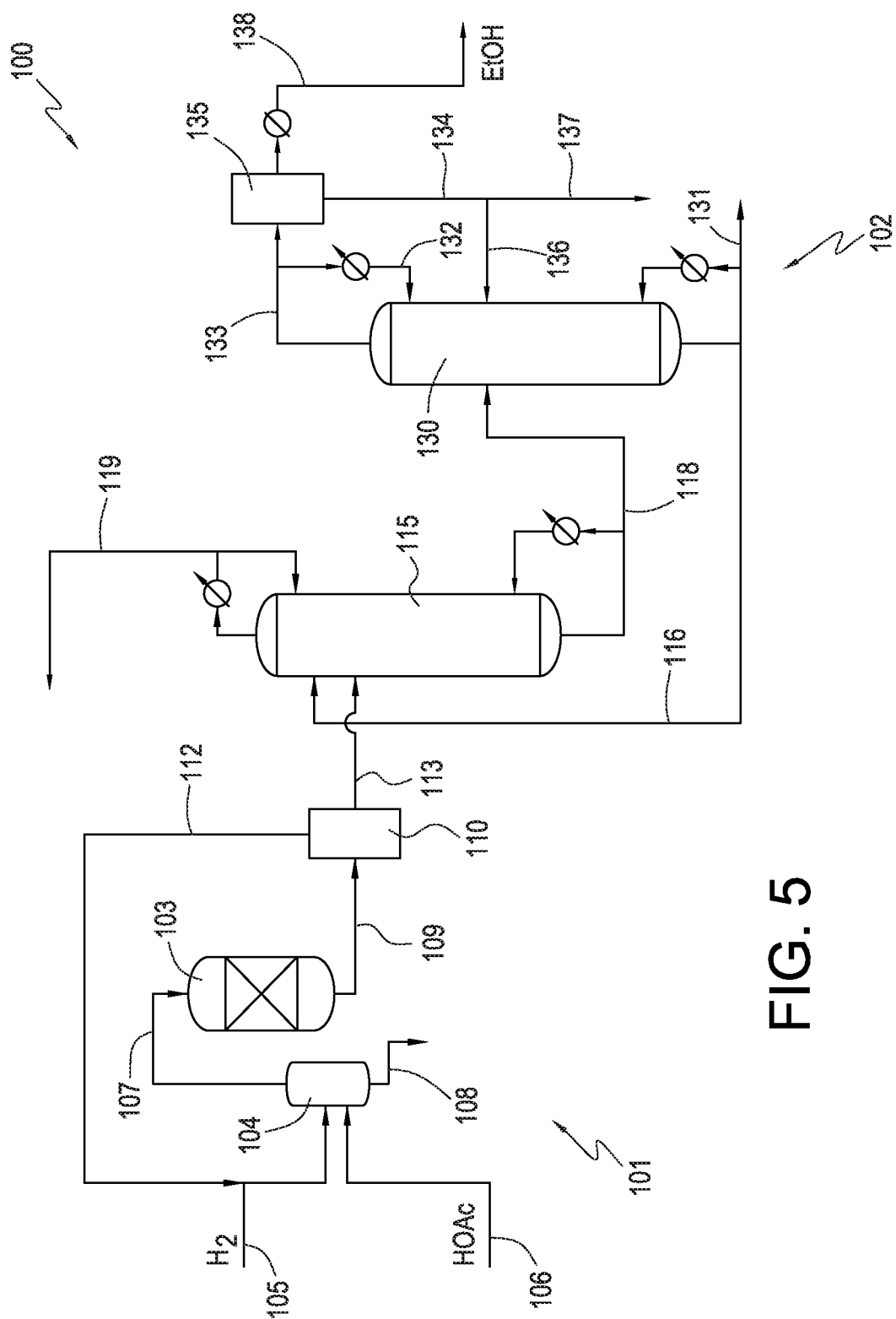
FIG. 5 is a schematic diagram of an ethanol production system with multiple distillation columns to recover ethanol from a stream that comprises acetic acid and low concentrations of ethyl acetate in accordance with one embodiment of the present invention.

When the first residue in line 118 comprises low amounts of acetic acid and/or there is no esterification within first residue, such that the ethyl acetate concentration is less than 50 wppm, third column 140 may be optional and removed as shown in FIG. 5. Thus, ethanol mixture stream 138 from the water separator 135 may be the ethanol product and no ethyl acetate recycle stream is required.

Depending on the amount of water and acetic acid contained in the second residue it may be desired to treat the second residue in line 131 in one or more of the following processes. A suitable weak acid recovery system is described in US Pub. No. 2012/0010446, the entire contents and disclosure of which is hereby incorporated by reference. When the second residue comprises primarily acetic acid, e.g., greater than 70 wt. %, the residue may be recycled to the reactor without any separation of the water. When the second residue comprises from 50 to 70 wt. % acetic acid, the second residue may be separated into an acetic acid stream and a water stream. Acetic acid may also be recovered in some embodiments from the first residue. The residue may be separated into the acetic acid and water streams by a distillation column or one or more membranes. If a membrane or an array of membranes is employed to separate the acetic acid from the water, the membrane or array of membranes may be selected from any suitable acid resistant membrane that is capable of removing a permeate water stream. The resulting acetic acid stream optionally is returned to reactor 103. The resulting water stream may be used as an extractive agent or to hydrolyze an ester-containing stream in a hydrolysis unit.

In other embodiments, for example where the second residue in line 131 comprises less than 50 wt. % acetic acid, possible options include one or more of: (i) returning a portion of the residue to reactor 103, (ii) neutralizing the acetic acid, (iii) reacting the acetic acid with an alcohol, or (iv) disposing of the residue in a waste water treatment facility. It also may be possible to separate a residue comprising less than 50 wt. % acetic acid using a weak acid recovery distillation column to which a solvent (optionally acting as an azeotroping agent) may be added. Exemplary solvents that may be suitable for this purpose include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. When neutralizing the acetic acid, it is preferred that the residue in line 131 comprises less than 10 wt. % acetic acid. Acetic acid may be neutralized with any suitable alkali or alkaline earth metal base, such as sodium hydroxide or potassium hydroxide. When reacting acetic acid with an alcohol, it is preferred that the residue comprises less than 50 wt. % acetic acid. The alcohol may be any suitable alcohol, such as methanol, ethanol, propanol, butanol, or mixtures thereof. The reaction forms an ester that may be integrated with other systems, such as carbonylation production or an ester production process. Preferably, the alcohol comprises ethanol and the resulting ester comprises ethyl acetate. Optionally, the resulting ester may be fed to the hydrogenation reactor.

In some embodiments, when the second residue in line 131 comprises very minor amounts of acetic acid, e.g., less than 5 wt. % or less than 1 wt. %, the residue may be neutralized and/or diluted before being disposed of to a waste water treatment facility. The organic content, e.g., acetic acid content, of the residue beneficially may be suitable to feed microorganisms used in a waste water treatment facility.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

The ethanol product produced by the processes of the present invention may be an industrial grade ethanol or fuel grade ethanol. Exemplary finished ethanol compositional ranges are provided below in Table 6.

TABLE 6

FINISHED ETHANOL COMPOSITIONS

| Component | Conc. (wt. %) | Conc. (wt. %) | Conc. (wt. %) |
|---|---|---|---|
| Ethanol | 85 to 99.9 | 90 to 99.5 | 92 to 99.5 |
| Water | <12 | 0.1 to 9 | 0.5 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

The finished ethanol composition produced by the embodiments of the present invention may be used in a variety of applications including applications as fuels, solvents, chemical feedstocks, pharmaceutical products, cleansers, sanitizers, hydrogen transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene.

While the invention has been described in detail, modifications within the spirit and scope of the invention will be readily apparent to those of skill in the art. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with one or more other embodiments, as will be appreciated by one of skill in the art. Furthermore, those of ordinary skill in the art will appreciate that the foregoing description is by way of example only, and is not intended to limit the invention.

We claim:

1. A process for producing ethanol comprising:
hydrogenating acetic acid and/or an ester thereof in a reactor in the presence of a catalyst to form a crude ethanol product;
separating a portion of the crude ethanol product in a first extractive distillation column to yield a first distillate comprising acetaldehyde and ethyl acetate, and a first residue comprising ethanol, and water;
separating a portion of the first residue in a second distillation column to yield a second residue comprising water and a vapor overhead comprising ethanol and water;
removing water from a portion of the vapor overhead to yield an ethanol mixture stream; and
separating at least a portion of the ethanol mixture stream in a third distillation column to yield a third distillate comprising 70 to 90 wt. % ethanol and a third residue comprising ethanol and less than 8 wt. % water;
wherein the third distillate is fed to the first column and at least a portion of the first distillate is returned to the reactor.

2. The process of claim 1, further comprising introducing an extractive agent to the first column.

3. The process of claim 2, wherein the extractive agent comprises water.

4. The process of claim 2, wherein the extractive agent is derived from a portion of the second residue.

5. The process of claim 2, wherein the extractive agent is derived from the water removed from the portion of the vapor overhead.

6. The process of claim 1, wherein the first residue comprises from 50 to 99.9% of the ethanol from the crude ethanol product.

7. The process of claim 1, wherein the first residue comprises from 80 to 100% of the water from the crude ethanol product.

8. The process of claim 1, wherein the first residue comprises from 85 to 100% of the acetic acid from the crude ethanol product.

9. The process of claim 1, wherein the first distillate further comprises at least one component selected from the group consisting of diethyl acetal, acetone and ethyl acetate.

10. The process of claim 1, further comprising:
separating the crude ethanol product in a separator to form a liquid stream comprising ethanol and a vapor stream comprising hydrogen.

11. The process of claim 10, wherein the separator comprises one or more membranes.

12. The process of claim 10, wherein the separator comprises a flasher or a knock out pot.

13. The process of claim 1, wherein the first distillate is separated with an extractant in an extractive distillation column to form an extract comprising ethanol and a raffinate comprising acetaldehyde, and further wherein the raffinate is returned to the reactor.

14. The process of claim 13, wherein the extractant comprises one or more of benzene, propylene glycol or cyclohexane.

15. The process of claim 13, wherein the extractant comprises water.

16. The process of claim 13, wherein the extract is combined with either the third residue, the second distillate, or the first residue.

17. A process for purifying a stream to yield ethanol comprising:
providing an ethanol mixture stream comprising from 90 to 99.9 wt. % ethanol, 0.0001 to 10 wt. % ethyl acetate, 0.0001 to 10 wt. % acetaldehyde, 0.0001 to 10 wt. % water, 0.0001 to 10 wt. % acetal,
separating the ethanol mixture stream in a distillation column to concentrate ethyl acetate in the distillate and recover ethanol in the residue, wherein the distillate comprises from 70 to 99 wt. % ethanol and the residue comprises from 80 to 99.5 wt. % ethanol.

18. The process of claim 17, further comprising separating the distillate with an extractant in an extractive distillation column to form an extract comprising ethanol and a raffinate comprising ethyl acetate.

19. The process of claim 18, wherein the extract is combined with the residue.

20. The process of claim 17, wherein the distillate comprises from 1 to 30 wt. % ethyl acetate.

* * * * *